United States Patent

Rantanen

Patent Number: 5,576,552
Date of Patent: Nov. 19, 1996

[54] IMAGE PLATE FOR INTRAORAL DENTAL RADIOGRAPHY

[75] Inventor: Matti Rantanen, Kirkonummi, Finland

[73] Assignee: Orion-Yhtyma OY, Espoo, Finland

[21] Appl. No.: 416,777

[22] PCT Filed: Oct. 26, 1993

[86] PCT No.: PCT/FI93/00439

§ 371 Date: Apr. 10, 1995

§ 102(e) Date: Apr. 10, 1995

[87] PCT Pub. No.: WO94/10605

PCT Pub. Date: May 11, 1994

[30] Foreign Application Priority Data

Oct. 27, 1992 [FI] Finland ................. 924873

[51] Int. Cl.6 ............................ G03B 42/04
[52] U.S. Cl. ............ 250/484.4; 250/581; 378/169
[58] Field of Search .................. 250/484.4, 581; 378/169

[56] References Cited

U.S. PATENT DOCUMENTS 1,631,497  6/1927  Marler ..................... 378/169
5,466,561  11/1995 Rantanen ................... 430/347

FOREIGN PATENT DOCUMENTS

| 0100483 | 2/1984 | European Pat. Off. | ............... 250/581 |
| 920937 | 3/1992 | Finland . | |
| 124931 | 4/1919 | United Kingdom | ................... 378/169 |

Primary Examiner—Constantine Hannaher
Attorney, Agent, or Firm—Pennie & Edmonds

[57] ABSTRACT

The invention relates to an image plate (1) for intraoral dental radiography which can be closed within a cover through which X-rays can pass, where the plate is retained during the X-raying and from where the plate can be removed after the X-raying in order to read the picture. According to the invention the edges of the image plate (1) are equipped with a protective frame (2) projecting from the plane of the plate surface at least on the image side of the plate. The frame may be formed as a continuous cover frame (2) surrounding the edges of the frame, consisting of two opposite frame-like portions (7) pressed together and optionally identical. The purpose of the frame (2) is to protect the image plate (1) against scratches or similar damages as the plate is being handled and read.

8 Claims, 1 Drawing Sheet

IMAGE PLATE FOR INTRAORAL DENTAL RADIOGRAPHY

FIELD OF THE INVENTION

This invention relates to an image plate for intraoral dental radiography which can be closed into a cover through which X-rays can pass and in which the plate is kept during the X-raying, and from which the plate can be removed after the X-raying in order to read the picture.

BACKGROUND OF THE INVENTION

A film in a plastic or a cardboard package or an image plate in a cassette have been used so far in intraoral dental radiography. The image plate has been either free in the openable cassette or fixed by glueing to a rigid cassette equipped with a slide plate.

U.S. Pat. No. 5,466,561 describes a solution, in which the image plate is placed into a cover letting through X-rays but not visible light, which comprises a closed protective bag of plastic film. The image plate including the bag-like cover is thinner and thus more pleasant to the patient than a cassette containing the image plate, and compared to a conventional intraoral film, it has the advantage of a lower sensitivity to visible light.

According to U.S. Pat. No. 5,466,561 the image plate is placed into the cover as such for the time of the X-raying. In this connection there have been problems caused by scratches on the plastic film on the image surface of the plate when the plate is being handled and scanned, as well as finger prints on the image surface which will be visible on the resulting picture. Besides the image surface, the edges of the plate have been easily damaged and broken. The edges of the plate have in fact been protected with a coated plastic film, however this has proved an unsufficient protection. When the edge is broken, the RIM substance within the plate, such as a poisonous barium compound, will appear, and may be hazardous to the patient or the person who handles the plate. An unprotected RIM substance does not resist sterilization carried out with ethanol for instance, the entire plate being destroyed in that case. The operating life of the image plate may be shortened by these wear and damage problems.

SUMMARY OF THE INVENTION

The purpose of this invention is to provide a solution which eliminates the above problems related to image plates so far. The image plate of the invention is characterized by its edges being equipped with a protective frame, which projects beyond the plane of the plate surface at least on the image side of the plate.

The frame according to the invention constitutes a shock-resistant cover for the easily damaged edges of the image plate. Moreover, the frame projecting from the image surface provides efficient prevention of abrasive and scratching wear of the surface and consequently prevents a deterioration of the image quality entailed by this. The projecting frame is also easy to grip, so that fewer detrimental finger prints are left on the image surface. Yet, the relatively narrow frame does not increase the outer dimensions of the image plate significantly, nor does it reduce the dimensions of the image surface and the pictures obtained noticeably.

The frame according to the invention advantageously forms a continuous cover frame surrounding the edges of the image plate. Such a cover frame may consist of two opposite frame-shaped portions connected to each other by pressing. The plate edges are then locked inbetween the interconnected frame portions.

The opposite interconnected portions of the cover frame may be identical, which is advantageous for instance in view of a production by means of mould casting. The design of the cover may be the same as in known slide frames, the halves of which are equipped with alternating recesses and matching projections, so that the projections and the recesses coincide and engage when the halves are being pressed against each other. However, snapping or glueing are also possible means for connecting the portions of the cover frame according to the invention.

According to a preferred emboidment of the invention, the frame is provided with a guide at least at one end of the image plate for mutual positioning of the plate and a drive gripping it as the picture is being read. The control may consists of a guide pin in the frame or any similar projection parallel to the surface of the image plate.

According to the invention the frame of the image plate is preferably of a flexible plastic material such as polypropene for instance. Such a frame is easy to produce by mould casting, it has a light structure and is resistant to shocks and bending. The plastic frame glides easily in a bag-like plastic cover, in which the image plate is kept during X-raying, and also resists sterilizing of the image plate with ethanol.

BRIEF DESCRIPTION OF THE DRAWINGS

The invention is described in further detail below with the aid of an example, with reference to the enclosed drawing, in which.

DETAILED DESCRIPTION OF THE INVENTION

Figure 1:
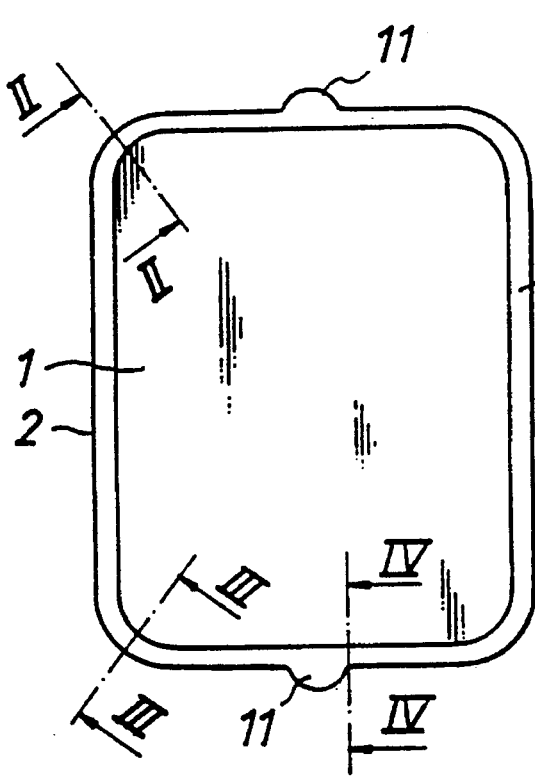
FIG. 1 is a view of an image plate according to the invention equipped with a cover frame.

FIGS. 1 to 4 present an image plate 1 intended for intraoral dental radiography by using RIM technique, the edges of the plate being provided with a continuous protective frame 2 encircling the plate. The image plate 1 is a fairly rigid approx. 1 mm thick layer plate, in which the surface layer on the image side 3 is made of plastic film, below this there is a thin and fairly soft layer containing a RIM substance such as barium compound, below this there is a rigid plastic layer and at the bottom a layer of metal, such as iron or steel, which can be gripped with a magnet. These layers placed on top of each other in the image plate 1 are not illustrated in the drawing.

Figure 2:
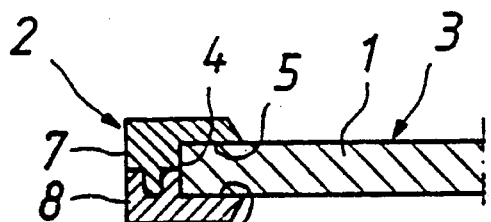
FIGS. 2, 3 and 4 show the cover frame at the edge of the image plate as sections II—II, III—III and IV—IV respectively of FIG. 1.
Figure 3:
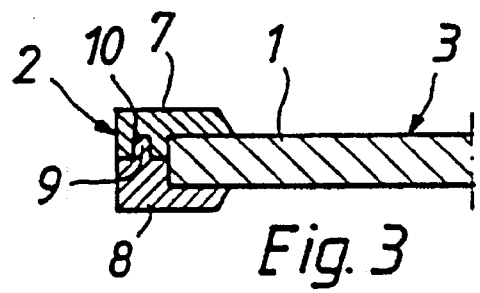
Figure 4:
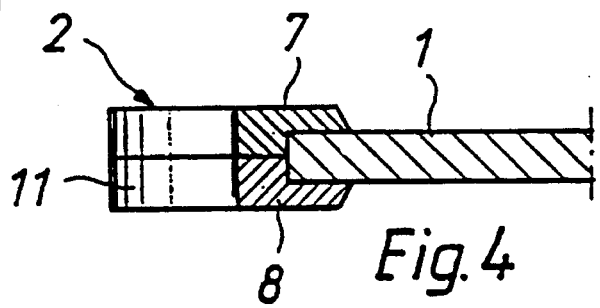

The cover frame 2 of the plate consists of a plastic frame, which, as shown in FIGS. 2 to 4, covers the edge surfaces 4 of the plate and the narrow edge zone 5, 6 on the upper and lower surfaces of the plate, whereby the frame projects to a certain extent from the plane of the plate surface on either side of the plate. This provides protection for the upper side of the plate, i.e. the image side 3, against abrasive and scratching wear of the plastic coating and finger prints.

The cover frame 2 consists of two opposite frame-shaped identical portions 7, 8, which are interconnected with pin-like projections 9 and matching recesses 10. The projections 9 and the recesses 10 have been disposed in the frame portions 7, 8 in such a way that, as the portions are fitted against each other, the projections and the recesses coincide and engage into each other when the portions are being pressed together.

FIGS. 1 and 4 show the guide pins 11 fitted in the cover frame 2, the pins consisting of projections parallel to the plate surfaces at opposite ends of the plate. As the plate 1 is being scanned, a magnet in the scanner drive grips the bottom steel layer of the plate, and the guide pin 11 provides the necessary mutual positioning of the plate and the drive. The plate is read with a laser beam in a manner known per se in a space protected against the light of the reader.

Figure 5:
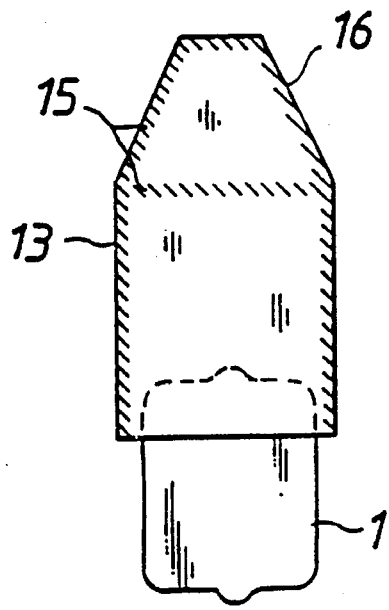
FIG. 5 is a view of the image plate being inserted into the inner bag included in the cover and FIG. 6 shows the image plate closed within the cover, which consists of an inner bag and a surrounding outer bag.
Figure 6:
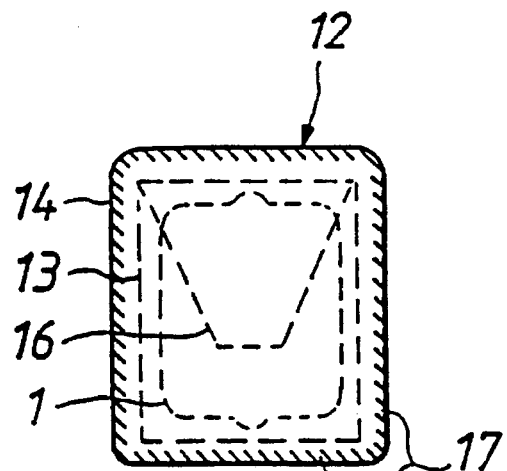

FIGS. 5 and 6 illustrate the cover 12, into which the image plate 1 of FIGS. 1 to 4 is closed for the time of the X-raying, and from which it is removed after the X-raying in order to read the picture. The cover 12 consists of an opaque inner bag 13 according to FIG. 5 and of an outer bag 14 of plastic film surrounding the inner bag as in FIG. 6. The inner bag 13 may be a black-couloured plastic film, which is shaped and jointed along seam lines 15 so as to form a lug 16, which is bent towards the rest of the bag before being closed into the outer bag 14. The end of the inner bag 13, at which the image plate is inserted into the bag as shown in FIG. 5, remains open. The outer bag 14, which may be of any transparent or opaque plastic material, is closed with a seam 17 encircling the bag.

When the X-raying has been carried out, the outer bag 14 is first removed by tearing. After this, the image plate 1 is inserted into a space inside the inner bag 13 which is protected against the light from the reader, and here the plate grips the scanner drive through the open end of the bag under the control of the guide pin 11. Finally the inner bag 13 is removed from the reader by pulling the lug 16, the plate 1 being ready for reading.

It is obvious to a person skilled in the art that the various embodiments of the invention are not restricted to the example above, but may vary within the scope of the enclosed claims.

I claim:

1. An image recording means for intraoral dental radiography, comprising an image plate closed within a cover permeable to X-rays, said plate being adapted to be removed from said cover after the X-raying to let the image as recorded to be read from the plate, the edges of said plate being equipped with a protective frame projecting from the plane of the surface of the plate at least on the side of the plate on which the image is recorded.

2. The image recording means of claim 1, wherein the image plate further comprises a continuous frame surrounding the edges of the plate.

3. The image recording means of claim 2, wherein the frame consists of two opposite frame-shaped portions, which have been interconnected by pressing.

4. The image recording means of claim 3, wherein the portions of the frame are identical.

5. The image recording means of claim 1, wherein the frame is equipped with a projection at least at one end of the image plate for mutual positioning of the plate with a scanner drive gripping the plate as the image is being read.

6. The image recording means of claim 5, wherein said projection is parallel to the surface of the image plate.

7. The image recording means of claim 1, wherein the frame is of a flexible plastic material.

8. The image recording means of claim 1, wherein the cover within which the image plate is closed consists of an opaque inner bag and an outer bag of plastic film surrounding the inner bag.

* * * * *